United States Patent [19]

Wolter

[11] Patent Number: 4,794,918

[45] Date of Patent: Jan. 3, 1989

[54] BONE PLATE ARRANGEMENT

[76] Inventor: Dietmar Wolter, Lohm/e,uml/u/hlenstrasse 5, 2000 Hamburg 1, Fed. Rep. of Germany

[21] Appl. No.: 859,653

[22] Filed: May 5, 1986

[30] Foreign Application Priority Data

May 6, 1985 [DE] Fed. Rep. of Germany ... 8513288[U]

[51] Int. Cl.⁴ .............................................. A61F 5/04
[52] U.S. Cl. ......................... 128/92 VP; 128/92 YL; 128/92 YF; 128/92 VS
[58] Field of Search ......... 128/92 YP, 92 YL, 92 YF, 128/92 VS

[56] References Cited

U.S. PATENT DOCUMENTS

| | | | |
|---|---|---|---|
| 3,244,170 | 4/1966 | McElvenny | 128/92 YP |
| 3,659,595 | 5/1972 | Haboush | 128/92 YL |
| 3,779,240 | 12/1973 | Kondo | 128/92 YP |
| 3,842,825 | 10/1974 | Wagner | 128/92 VS |
| 4,388,921 | 6/1983 | Sutter et al. | 128/92 YP |
| 4,408,601 | 10/1983 | Wenk | 128/92 YP |
| 4,429,690 | 2/1984 | Angelino-Dievani | 128/92 YP |
| 4,473,069 | 9/1984 | Kolmert | 128/92 YP |
| 4,484,570 | 11/1984 | Sutter et al. | 128/92 YP |
| 4,503,848 | 3/1985 | Caspar et al. | 128/92 YP |

FOREIGN PATENT DOCUMENTS 2519857  7/1983  France .

Primary Examiner—Stephen G. Pellegrino
Assistant Examiner—Colleen Reilly
Attorney, Agent, or Firm—Chilton, Alix & Van Kirk

[57] ABSTRACT

A bone plate arrangement consists of a bone plate (1), at least one bone screw (3) and a cover plate (5, 22, 30, 34, 38) which covers the head (4, 21, 26) of the bone screw and is to be screwed to the bone plate. Devices for fixing the direction of the bone screw (3) relative to the bone plate (1) are provided. These devices consist, on the one hand, of a seat which, though indifferent with respect to direction, laterally fixes the screw head on the bone plate and, on the other hand, of a positive of frictional connection betwen the screw head and the cover plate, produced by mutual engagement of the raises and recesses. The cover plate is laterally fixed relative to the bone plate.

12 Claims, 2 Drawing Sheets

BONE PLATE ARRANGEMENT

DESCRIPTION

The invention relates to a bone plate arrangement, consisting of a bone plate, at least one bone screw and a cover plate which covers the head of the bone screw and is to be screwed to the bone plate and has devices for fixing the direction of the bone screw relative to the bone plate.

Bone plates are used in osteosynthesis for bridging the fracture. They are joined to the fragments by means of bone screws. In a known bone plate arrangement of the abovementioned type (U.S. Pat. No. 3,842,825), four screws in a rectangular arrangement are provided on one end of a bone plate.

Their heads are covered by a common cover plate which is to be screwed to the bone plate. This cover plate presses the screw heads, provided with a flat lower surface, against a seating face provided for this purpose on the bone plate. Between the square-shaped screw heads, a bolt is seated which is arranged on the cover plate and prevents rotation of the screw heads. As a result, the screws are not only secured in their intended position but are also held parallel to one another. This is intended to counteract loosening of the screws. However, the idea of forcing all the screws belonging to one group into a parallel position is not compatible with the requirements in practice, because it must be possible to align every screw independently of the others in accordance with the particular anatomic conditions found and the position of the fracture. Securing by means of a bolt located between the square screw heads also leads to a hardly tolerable thickness of the arrangement.

In another known arrangement (FR-A No. 2,519,857), a securing disc, which partially covers the screw heads and prevents the screws from migrating out of their intended position, can be screwed on in the middle between a group of three bone screws. Here again, the screws are forced into a substantially predetermined direction, since the screw heads and the bores provided for them in the bone plate interact via an acute conical seat. Those arrangements have gained wide acceptance in practice in which the head of the bone screw faces the bone plate with a spherical seating surface which interacts with a conical or likewise spherical seating surface in the bore of the bone plate, this arrangement permitting any desired angular setting of the screw relative to the bone plate.

It is the object of the invention to provide a bone plate arrangement of the abovementioned type, which secures the screws in their intended position without forcing them into a fixed direction, but the osteosynthesis union nevertheless being provided with greater rigidity.

According to the invention, this is achieved when the bone plate interacts with the screw head by means of a seat which is indifferent with respect to direction but provides lateral fixing, and the cover plate screwed to the bone plate presses against the screw head via mutually engaging raises and recesses.

In fact, as discovered by the invention, positively interacting seating surfaces on the bone plate and on the screw head are not necessary in order to join these to one another in a directionally rigid manner. Rather, an extensive frictional connection, which can be influenced to the desired degree by suitable surface shaping, is sufficient in many cases. For example, the screw head can be fixed under the pressure of the cover plate by interacting roughnesses of the screw head or of the bone plate seat or of the cover plate. In another embodiment of this concept, a screw head with a spherical seating surface can be pressed into a pointed conical bore of the bone plate and thus fixed.

It is particularly advantageous when the cover plate, in its state screwed to the bone plate, is laterally immovable, because the screw head is shaped in such a way that its surface parts interacting with the cover plate must execute a lateral relative movement when the bone screw is pivoted relative to the bone plate. As a result, in addition to the fixed point formed in the bone plate seat, a further fixed point is formed on the screws, which prevents them from a free pivoting movement relative to the plate.

In a further advantageous embodiment of the invention, the screw head is bounded on the upper side at least partially by a spherical surface which is concentric with the lower spherical surface of the head, the cover plate having a recess or raise interacting with this surface. In this case, the screw head is fixed on the bone plate or cover plate exclusively by friction. Measures which increase friction, for example of the type already mentioned above, can be advantageous in this connection.

In a further embodiment of the invention, the upper side of the head and the cover plate interact via at least one spherical surface, the centre of which does not coincide with the pivoting centre of the screw, but with a seat formed by the plate. According to the invention, one of the two parts is intended then to interact with the spherical surface formed by the other part via contact points which are located on a spherical surface of the same diameter, in particular via an annular edge. The result of this arrangement is that, in the event of a pivoting movement of the screw relative to the bone plate, the centres of the two spheres must laterally shift relative to one another, which is only possible if the cover plate shifts relative to the bone plate, but this can easily be prevented by the friction of the two plates against one another.

The invention has the advantage that the implant union consisting of screws and the osteosynthesis plate is very rigid within itself. This is of value particularly when the screws can be driven only through the cortex layer immediately adjacent to the bone plate but not through the opposite cortex layer.

The invention is explained in more detail below by reference to the drawing, which illustrates advantageous embodiment examples and in which.

Figure 1:
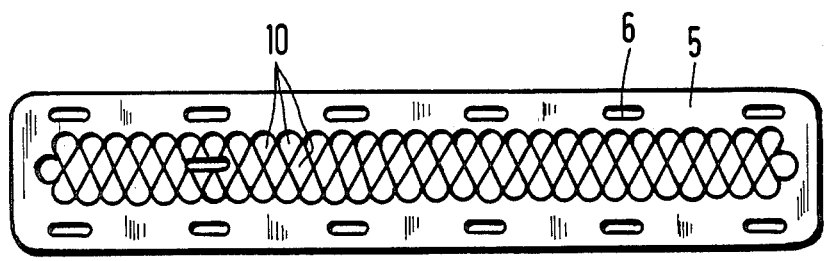
FIG. 1 shows a plan view of the underside of the cover plate.

The bone plate 1, which can be of known type and may also be connected to further implant components, contains passage holes 2 for bone screws 3, the heads 4 of which are located on the side of the bone plate 1 facing away from the bone or wholly or partially in the bores 2 and are of rounded convex form on their upper side. The screws are pivotable up to a certain extent in the bores. The bone plate 1 is associated with the cover plate 5 which can have essentially the same outline or is smaller. In most cases, it can be made somewhat thinner, if the bone plate 1 is left to cope with the major part of the flexural stress. However, with a view to the flexurally rigid joining of the two plates, as explained later, it is also possible to make the two plates of approximately the same thickness and, instead, to make the bone plate 1 thinner than has been usual hitherto, so that both plates participate in coping with the flexural stresses.

The cover plate 5 contains a large number of passage holes 6 which are formed as slots with the longer axis located in the longitudinal direction of the plate. Preferably, they are predominantly or exclusively located in the vicinity of the edge. However, instead or additionally, it is also possible, for example, to provide a central arrangement as indicated at 7.

The passage holes 6 in the cover plate 5 are associated with threaded holes 8 at the same position in the bone plate 1, so that the two plates can be joined to one another by means of a plurality of screws 9 with a two-dimensional fixing effect and can be tensioned against one another.

In that central strip of the underside of the cover plate 5 which can make a connection with the heads 4 of the bone screws 3, a grid, covering the surface, of recesses 10 is provided which immediately adjoin one another and—if they are imagined originally to have a circular outline—mutually overlap, the boundary ribs formed between them being shown in FIG. 1. They are arranged so closely together that each screw head will with a high probability "find" a recess into which it can penetrate in such a way that it can thus interact with the recess in the sense of mutual lateral fixing. However, this is not absolutely necessary since adequate lateral fixing is frequently accomplished even if a screw head does not fit precisely into a recess but interacts with one or more boundary ribs between the recesses, because even then, due to the solid mutual clamping of the two plates, such a high friction is generated between the cover plate and the particular screw head that the latter is virtually immovably fixed relative to the cover plate. It is obvious that, as a variation of the embodiment shown, the cover plate surface and the screw head surface can be provided with a finer grid of raises and recesses, if this appears to be desirable for the purpose of more secure mutual fixing.

The cover plate therefore not only prevents migration of the screws 3 out of the osteosynthesis arrangement but also provides the latter with greater rigidity. Since, in fact, the screws 3 are laterally fixed not only on the underside of their heads at 11 but also on the upper side of the heads at 12, they are not readily able to pivot relative to the bone plate 1. They can therefore not yield by such pivoting to a relative displacement between the bone plate 1 and the associated bone.

Figure 2:
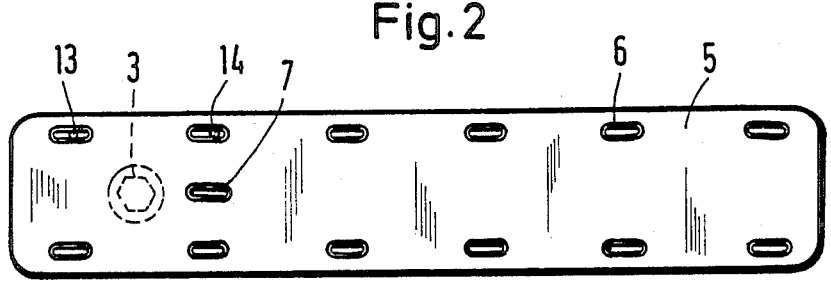
FIG. 2 shows a plan view of the upper side of the cover plate.
Figure 3:
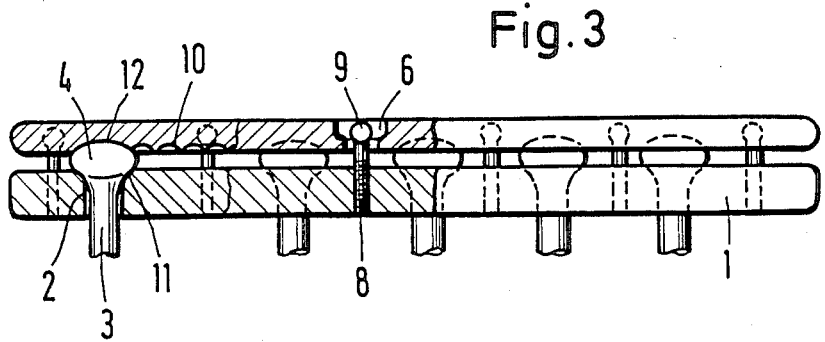
FIG. 3 shows a side view, partially in section, of the implant consisting of the osteosynthesis plate, cover plate and screws.

If the bone plate 1 together with the cover plate 5 is curved to match the configuration of the bone, the passage holes 6 and threaded holes 8, which were mutually aligned in the plane condition of the plates, are displaced relative to one another in the longitudinal direction. Allowance for this fact is made by the design of the passage holes 6 as slots, as illustrated in FIG. 2 by the different positions of the screw cross-sections 13 and 14.

The smoother outer surface of the cover plate 5 reduces irritation of the surrounding tissue and the risk of metallosis. The more rigid implant union also reduces the likelihood of metal abrasion by internal relative movements and thus likewise the risk of metallosis, and in addition the surrounding tissue is largely protected by the cover plate from the regions where metal abrasion can occur.

FIGS. 4 to 12, explained below, illustrate various arrangements for producing an effective angular fixing between the bone screw 3 and the bone plate 1.

Figure 4:
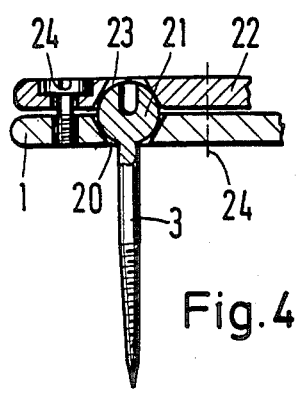
FIGS. 4 to 13 show further embodiment examples in a diagrammatic representation.

According to FIG. 4, the passage hole 20 in the bone plate 1 is made conical, with an acute cone angle of 10°-30°, and with further preference smaller than 25°. This interacts with the spherical screw head 21. For interaction with the screw head 21, the cover plate 22 likewise has an acute conical bore 23. When the cover-plate is tensioned by means of the screws 24 against the bone plate 1, the screw head 21 is pressed into the conical bores 20 and 23 and is thus fixed under extensive friction. The fixing is here independent of the particular angular position of the screw head. The cone angles are selected such that sufficient clamping is accomplished.

In this connection (as also in the other examples), the bores or recesses do not have to be conical. The only important point for the effect of increasing friction is that the common tangent in the contact point between the screw head surface and the bore/recess surface assumes a sufficiently small angle with the direction in which the cover plate 22 is tensioned against the bone plate. For example, an annular edge, as shown at 25 in FIG. 5, also suffices for this purpose. Such an edge can even produce particularly intensive friction and therefore be advantageous. The edge can also be of polygonal shape and thus form a relatively small number of sharp contact points.

Figure 5:
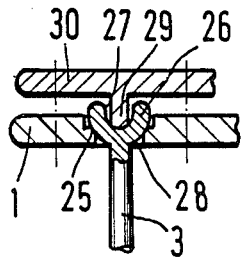

The screw head 26 of the illustrative embodiment in FIG. 5 contains a recess 27 with a bottom, of which the centre point of curvature coincides more or less with the centre point of curvature of the spherical surface 28 bounding the underside of the screw head. This interacts with a peg 29 of the cover plate 30.

The designs according to FIGS. 4 and 5 are identical to the extent that the screw head interacts not only with the bone plate 1 but also with the cover plate 22, 30 via spherical surfaces which have a common centre point, so that the particular angular position of the screw is irrelevant to the magnitude of the frictional force. It is to be understood that minor deviations from the spherical form can frequently be disregarded in this connection.

Surface roughness can increase friction and hence be advantageous. For example, it can have been produced in such a way that the spherical screw head surface is composed of a multiplicity of annular grooves.

Figure 6:
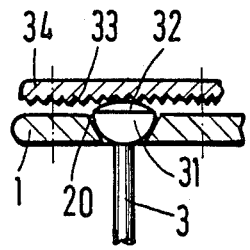

In the illustrative embodiment according to FIG. 6, the screw head is bounded on the underside by a spherical surface 31, whereas the bore 20 in the bone plate 1 is conical. Instead, other configurations of the seating surface are also conceivable which allow pivotability on the one hand and lateral positional fixing on the other hand, for example a conical surface on the side of the head and an all-round annular edge on the side of the bore.

On the upper side, the screw head is bounded by a spherical surface 32 which can but does not have to be concentric with the surface 31. It interacts with a lower surface 33, which is roughened by grooves, serrations or the like, of the cover plate 34. The latter is joined to the bone plate 1 by means of screws 24, to be laterally fixed. When pivoting forces act on the screw 3, the latter is prevented from pivoting by the holding moment which is generated between the contact points of the screw head with the bone plate on the one hand, and the cover plate on the other hand, the screw head trying to displace the cover plate laterally. This is counteracted by laterally rigid clamping of the cover plate to the bone plate. This lateral rigidity can be accomplished by arranging the screws 24 without play; however, in general even the fixing friction acting on these screws is already sufficient, even if more extensive play is provided. For this reason, the top surface 32 of the screw head is made in a more or less convex-spherical form, because a flat shape of the screw head would entail a tendency of the screw to align itself vertically relative to the cover plate. This can be prevented by a not unduly flat convex curvature. This also applies to other illustrative embodiments.

Figure 7:
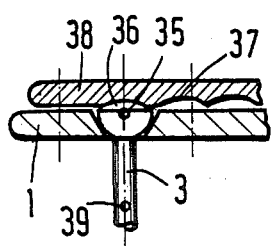
Figure 8:
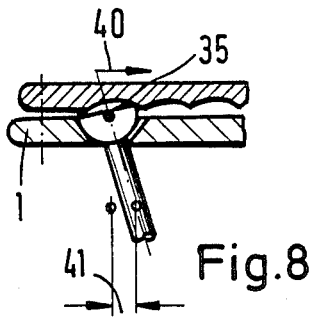
Figure 9:
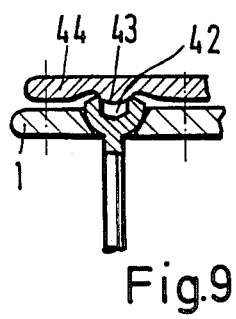

According to FIGS. 7 and 8, the screw head is fixed laterally rigidly relative to the bone plate by the interaction of spherical and conical surface, the centre point for pivoting being located along these surfaces at 35. The top surface 36 of the screw head is convex-spherical, matching a concave recess 37 in the cover plate 38. The centre point of the spherical surface 36 is indicated at 39. Pivoting of the screw, from the position according to FIG. 7 into that according to FIG. 8 entails a displacement of the centre 39 relative to the pivoting centre point 35, and this is possible without a substantial deformation resistance only if the cover plate 38 is displaced in the direction of the arrow 40 by the distance 41. However, this is prevented by the laterally rigid screwed connection of the cover plate 38 to the bone plate.

This functional mechanism is also the basis of the illustrative embodiments which follow. According to the illustrative embodiment in FIG. 9, the screw head has a recess 42, for example for the insertion of a hexagon socket key. This recess interacts with a spherical projection 43 of the laterally rigidly arranged cover plate 44.

Figure 10:
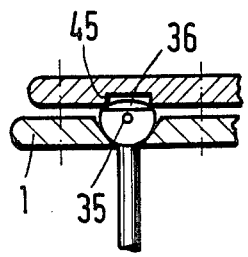

The illustrative embodiment according to FIG. 10 shows a screw head which is bounded on the top side (as in FIGS. 7 and 8) by a convex-spherical surface 36, the centre point of which does not coincide with the pivoting centre point 35 fixed by the lower surface. An annular edge 45 of the cover plate interacts with the spherical surface 36.

Figure 11:
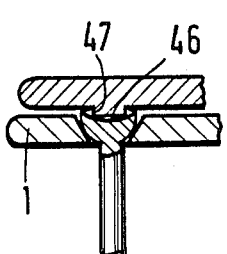

According to FIG. 11, the screw head is bounded on the top side by a concave-spherical surface 46, with which an annular edge 47 of the cover plate interacts.

Figure 12:
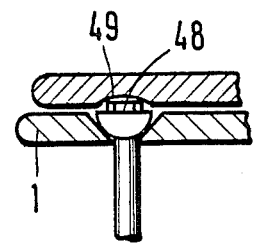

Finally, FIG. 12 shows an embodiment in which the screw head has a hexagon 48 on the top side for engagement of a key, the polygonal edge of the hexagon interacting with a concave-spherical surface 49 of the cover plate.

Figure 13:
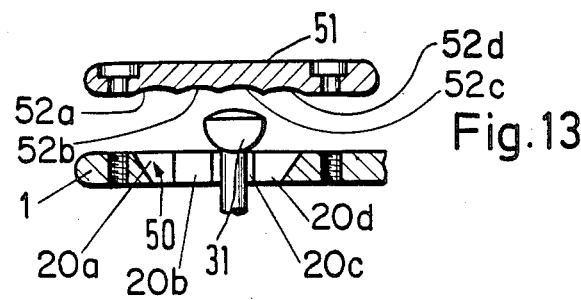

FIGS. 4 to 12 explained above illustrate only the functional principle; their arrangement can vary widely in an individual case. For example as shown in FIG. 13, the place of individual passage holes 20 in the bone plate 1 can be taken by a sequence of passage holes 20a, 20b, 20c, and 20d which supplement each other to give an elongate slot 50, and which are faced on the side of the cover plate 51 by a correspondingly arranged number of recesses 52a, 52b, 52c, and 52d. A cross sectional view taken along a plane perpendicular to the drawing plane of FIG. 13, showing the relationship between the bone plate, the seated screw head, and the tightened cover plate, would look like FIG. 7.

I claim:

1. A bone plate arrangement comprising:
    a bone plate including at least one bone screw hole having a center line and a seat on the upper side of the bone plate opposite the lower side adapted to face the bone, said seat having an acutely narrowing profile in the direction from the upper toward the lower side;
    a bone screw having a longitudinal axis, said bone screw adapted to pass through the bone screw hole into the bone and including a bone screw head having a generally convex seating surface which is contoured such that when the bone screw is fully inserted into the bone through the hole with the axis along a selected one of a range of angular orientations relative to said center line, the seating surface of the head is supported in said seat;
    a cover plate including means for engaging the bone plate so that the underside of the cover plate tightly engages the screw head; and
    said bone screw head and the underside of the cover plate having raises and recesses which mutually engage when the cover plate tightly engages the screw head so as to hold the head in fixed lateral relation to the bone plate and prevent pivoting thereof, whereby the bone screw axis is fixed in said selected angular orientation relative to the hole centerline.

2. A bone plate arrangement according to claim 1 wherein the seating surface of the screw head is spherical.

3. A bone plate arrangement according to claim 2, wherein the seating surface of the bone plate is conical.

4. A bone plate arrangement according to claim 2, wherein the screw head has an upper side at least partially defined by a convex spherical surface which is concentric with the spherical seating surface of the head, and the cover plate has a recess interacting with said upper side spherical surface.

5. A bone plate arrangement according to claim 1, wherein the underside of the cover plate includes said raises in the form of serration means for increasing friction between the mutually engaging surfaces of the bone screw head and the cover plate.

6. A bone plate arrangement according to claim 1 wherein the seating surface of the screw head is spherical.

7. A bone plate arrangement according to claim 1, further including means for adjusting the lateral position of the cover plate relative to the bone plate before the cover plate is drawn toward the bone plate.

8. A bone plate arrangement according to claim 7 wherein the upper surface of the head and the cover plate interact through at least one spherical surface having a first center point, wherein the bone screw head in the seat has a second center point, and wherein the first and second center points do not coincide.

9. A bone plate arrangement according to claim 7 wherein at least one of the interacting surfaces of the screw head, the bone plate and the underside of the cover plate include means for increasing friction between the interacting surfaces.

10. A bone plate arrangement according to claim 7, wherein at least one of the engaging surfaces of the screw head and cover plate is spherical about a first center point, and the screw head seating surface has a second center point about which the bone screw is pivotable, the second center point being different from said first center point.

11. A bone plate arrangement according to claim 10, wherein the bone screw head surface engaging the cover plate is convex spherical about one diameter and the engagement contact of the head on the cover plate lies on a concave spherical surface of the same diameter on the cover plate.

12. A bone plate arrangement according to claim 3, wherein the screw head has an upper side at least partially defined by a convex spherical surface which is concentric with the spherical seating surface of the head, and the cover plate has a recess interacting with said upper side spherical surface.

* * * * *